(12) United States Patent
Berry et al.

(10) Patent No.: US 11,291,838 B2
(45) Date of Patent: Apr. 5, 2022

(54) SYSTEMS AND METHODS FOR CONTROLLING BREATHING

(71) Applicant: Mayo Foundation for Medical Education and Research, Rochester, MN (US)

(72) Inventors: Brent M. Berry, Rochester, MN (US); Carlos B. Mantilla, Rochester, MN (US); Obaid Khurram, Chicago, IL (US); Soudabeh Kargar, Rochester, MN (US); Joseph D. Mozingo, Rochester, MN (US); Michal T. Kucewicz, Rochester, MN (US); Erik S. Daniel, Simi Valley, CA (US); Gary C. Sieck, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 25 days.

(21) Appl. No.: 16/643,343

(22) PCT Filed: Aug. 30, 2018

(86) PCT No.: PCT/US2018/048785
§ 371 (c)(1),
(2) Date: Feb. 28, 2020

(87) PCT Pub. No.: WO2019/046547
PCT Pub. Date: Mar. 7, 2019

(65) Prior Publication Data
US 2020/0254244 A1 Aug. 13, 2020

Related U.S. Application Data

(60) Provisional application No. 62/552,745, filed on Aug. 31, 2017.

(51) Int. Cl.
*A61N 1/36* (2006.01)
*A61B 5/08* (2006.01)
(Continued)

(52) U.S. Cl.
CPC .......... *A61N 1/3601* (2013.01); *A61B 5/0816* (2013.01); *A61B 5/389* (2021.01);
(Continued)

(58) Field of Classification Search
CPC ................ A61N 1/3601; A61N 1/3611; A61N 1/36034; A61N 1/025; A61N 1/0517;
(Continued)

(56) References Cited

U.S. PATENT DOCUMENTS 8,412,331 B2   4/2013 Tehrani et al.
2001/0018547 A1   8/2001 Meehlenburg et al.
(Continued)

OTHER PUBLICATIONS

Brancatisano et al., "Respiratory activity of posterior cricoarytenoid muscle and vocal cords in humans," J. Appl. Physiol. Respir. Environ. Exerc. Physiol., 1984, 57(4):1143-1149, 1984.
(Continued)

*Primary Examiner* — Tammie K Marlen
(74) *Attorney, Agent, or Firm* — Fish & Richardson P.C.

(57) ABSTRACT

This document describes methods and devices for using electrical stimulation to control physiological functions such as breathing of patients suffering from respiratory impairment. For example, this document describes methods and devices for generating effective breaths and airway protection by determining times and depths of breaths in accordance with physiological demand, and coordinating respiratory muscle stimulation with the breaths to control breathing.

18 Claims, 4 Drawing Sheets

(51) Int. Cl.
*A61B 5/00* (2006.01)
*A61N 1/02* (2006.01)
*A61N 1/05* (2006.01)
*A61B 5/389* (2021.01)

(52) U.S. Cl.
CPC .............. *A61B 5/686* (2013.01); *A61N 1/025* (2013.01); *A61N 1/0517* (2013.01); *A61N 1/0519* (2013.01); *A61B 5/7207* (2013.01)

(58) Field of Classification Search
CPC .... A61N 1/0519; A61B 5/389; A61B 5/0816; A61B 5/08; A61B 5/686; A61B 5/7207; A61B 5/0006; A61B 5/291; A61B 5/31; A61B 5/369; A61B 5/6822; A61B 2018/00839; A61B 2018/00327
See application file for complete search history.

(56) References Cited

U.S. PATENT DOCUMENTS

| | | |
|---|---|---|
| 2008/0103407 A1 | 5/2008 | Bolea et al. |
| 2010/0016749 A1 | 1/2010 | Atsma et al. |
| 2010/0125310 A1 | 5/2010 | Wilson et al. |
| 2011/0313484 A1 | 12/2011 | Hincapie Ordonez et al. |
| 2013/0030488 A1* | 1/2013 | Cho ................ A61N 1/3655 607/20 |
| 2015/0283382 A1 | 10/2015 | Denk et al. |
| 2015/0306384 A1 | 10/2015 | Denk et al. |
| 2017/0164893 A1 | 6/2017 | Narayan et al. |

OTHER PUBLICATIONS

DiMarco et al., "Inspiratory muscle pacing in spinal cord injury: case report and clinical commentary," J, Spinal Cord Med., 29(2):95-108, 2006.

International Search Report & Written Opinion in International Application No. PCT/US2018/048785 dated Nov. 11, 2018, 14 pages.

Jarosz et al., "Functional Electrical Stimulation in Spinal Cord Injury Respiratory Car," Top. Spinal Cord Inj. Rehabil., 18(4):315-21, Fall 2012.

Lanmüller et al., "Long-Term Electromyogram Recording from the Posterior Cricoarytenoid Muscle as a Potential Biological Trigger for Phrenic Pacing: Results of an Animal Study," Artificial organs, 23(9):860-8, Sep. 1999.

* cited by examiner

SYSTEMS AND METHODS FOR CONTROLLING BREATHING

CROSS-REFERENCE TO RELATED APPLICATIONS

This application is a National Stage application under 35 U.S.C. § 371 of International Application No. PCT/US2018/048785, having an International Filing Date of Aug. 30, 2018, which claims the benefit of U.S. Provisional Application Ser. No. 62/552,745, filed Aug. 31, 2017. The disclosure of the prior application is considered part of (and is incorporated by reference in) the disclosure of this application.

BACKGROUND

1. Technical Field

This document relates to methods and devices for using electrical stimulation to control physiological functions such as breathing. For example, this document relates to methods and devices for generating effective breaths and airway protection by determining times and depths of breaths in accordance with physiological demand, and coordinating respiratory muscle stimulation with the breaths to control breathing.

2. Background Information

Each year, approximately 10,000-12,000 people experience a spinal cord injury. Of this population, 50-60% of the spinal cord injuries are to the cervical spine, which can cause respiratory problems, and leads to 20-30% of deaths of patients one year after a spinal cord injury. Further, 40-80% of these patients also experience sleep disordered breathing, with 15% of the non-obese population experiencing sleep disordered breathing. With injury to the cervical portion of the spinal cord, control of the diaphragm can be limited, which plays a major role in controlling breathing.

SUMMARY

This document describes methods and devices for using electrical stimulation to control physiological functions such as breathing of patients suffering from respiratory impairment. For example, this document describes methods and devices for generating effective breaths and airway protection by determining times and depths of breaths in accordance with physiological demand, and coordinating respiratory muscle stimulation with the breaths to control breathing.

In one aspect, this disclosure is directed to a system for controlling breathing. The system can include a sensing electrode that senses electromyography (EMG) or electroneurogram (ENG) data from a throat muscle or nerve of a patient, a stimulation electrode that provides stimulation to a diaphragm of the patient, and an implantable medical device communicably coupled to the sensing electrode and the stimulation electrode. The implantable medical device can include a memory that is capable of storing computer executable instructions, and a processor that is configured to facilitate execution of the executable instructions stored in memory. In some cases, the instructions can cause the processor to receive the EMG or ENG data from the sensing electrode, detect an intent of the patient to take a breath from the EMG or ENG data, and deliver an electrical signal to the diaphragm via the stimulation electrodes when the intent of the patient to take a breath is detected. In some cases, the throat muscle can be a posterior cricoarytenoid muscle. In some cases, an intent of the patient to take a breath can be detected based on an initiation of a contraction of the neck muscle. In some cases, the electrical signal can include an onset delay. In some cases, the onset delay can correspond to a natural delay between the initiation of the contraction of the throat muscle and a contraction of the diaphragm during normal breathing. In some cases, the instructions can cause the processor to determine a magnitude of a contraction of the throat muscle. In some cases, the electrical signal can include an amplitude and the amplitude can correspond to the magnitude of the contraction of the throat muscle. In some cases, the instructions can cause the processor to detect a non-breath and inhibit delivering of electrical signals upon detecting the non-breath. In some cases, the non-breath can include coughing, chewing, movement of the neck, and/or swallowing.

In another aspect, this disclosure is directed to a method of controlling breathing. The method can include receiving, from a sensing electrode, electromyography (EMG) or electroneurogram (ENG) data from a throat muscle or a throat nerve of a patient, detecting, via a processor, an intent of the patient to take a breath from the EMG or ENG data, and delivering, via a stimulation electrode, an electrical signal to a diaphragm or a phrenic nerve of the patient when the intent of the patient to take a breath is detected. In some cases, the throat muscle can be a posterior cricoarytenoid muscle. In some cases, the intent of the patient to take a breath can be detected based on an initiation of a contraction of the throat muscle. In some cases, the electrical signal can include an onset delay. In some cases, the onset delay can correspond to a natural delay between the initiation of the contraction of the throat muscle and a contraction of the diaphragm during normal breathing. In some cases, the method can include determining a magnitude of a contraction of the throat muscle. In some cases, the electrical signal can include an amplitude and the amplitude can correspond to the magnitude of the contraction of the throat muscle. In some cases, the method can include detecting a non-breath and inhibiting delivery of electrical signals upon detecting the non-breath. In some cases, the non-breath is coughing, chewing, movement of the neck, and/or swallowing.

In another aspect, this disclosure is directed to an implantable medical device configured to be communicably coupled to a sensing electrode and a stimulation electrode. The implantable medical device can include a memory that is capable of storing computer executable instructions, and a processor that is configured to facilitate execution of the executable instructions stored in memory. In some cases, the instructions can cause the processor to receive electromyography (EMG) or electroneurogram (ENG) data from a throat muscle or nerve of a patient, detect an intent of the patient to take a breath from the EMG or ENG data, and deliver an electrical signal to a diaphragm of the patient when the breath is detected. In some cases, the throat muscle can be a posterior cricoarytenoid muscle. In some cases, the intent of the patient to take a breath can be detected based on an initiation of a contraction of the throat muscle. In some cases, the electrical signal can include an onset delay and the onset delay can correspond to a natural delay between the initiation of the contraction of the throat muscle and a contraction of the diaphragm during normal breathing.

Particular embodiments of the subject matter described in this document can be implemented to realize one or more of the following advantages. The methods and devices described herein can control breathing in a biocompatible and minimally invasive manner that provides prolonged use with minimal deterioration of efficacy. The timing and amplitude of each breath can be determined according to physiological demands to generate effective breaths in sync with natural breathing. The methods and devices described herein advantageously use electrical stimulation of the patient's own respiratory muscles and systems to facilitate breathing in a natural manner, as compared to mechanical ventilation. In some embodiments, the methods and devices described herein can also advantageously be used to maintain airway clearance (e.g., via coughing, sneezing, etc.), and/or other physiological functions such as swallowing, phonation, voiding, and the like. In some embodiments, the methods and devices described herein are fully automatic in that the stimulation of muscles for breathing and/or other functions result from the detection of activity of the patient's own nerves and/or muscles. Hence, it is advantageous that no manual intervention (e.g., from a rehab clinician) to help facilitate breathing and/or other functions is needed in some embodiments.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference numbers represent corresponding parts throughout.

DETAILED DESCRIPTION

This document describes methods and devices for using electrical stimulation to control physiological functions such as breathing of patients suffering from respiratory impairment. For example, this document describes methods and devices for generating effective breaths and/or airway protection by determining times and depths of breaths in accordance with physiological demand, and coordinating respiratory muscle stimulation with the breaths to control breathing.

With injury to the cervical portion of the spinal cord, control of the diaphragm can be limited, which plays a major role in controlling breathing. However, muscles above the cervical portion of the spinal cord can still maintain normal function. Accordingly, muscles above the cervical portion of the spine may be used to create a closed-loop system that provides stimulation to the diaphragm to control breathing.

The methods and devices described herein can control breathing in a biocompatible and minimally invasive manner that provides prolonged use with minimal deterioration of efficacy. The timing and amplitude of each breath can be determined according to physiological demands to generate effective breaths in sync with natural breathing.

Figure 1:
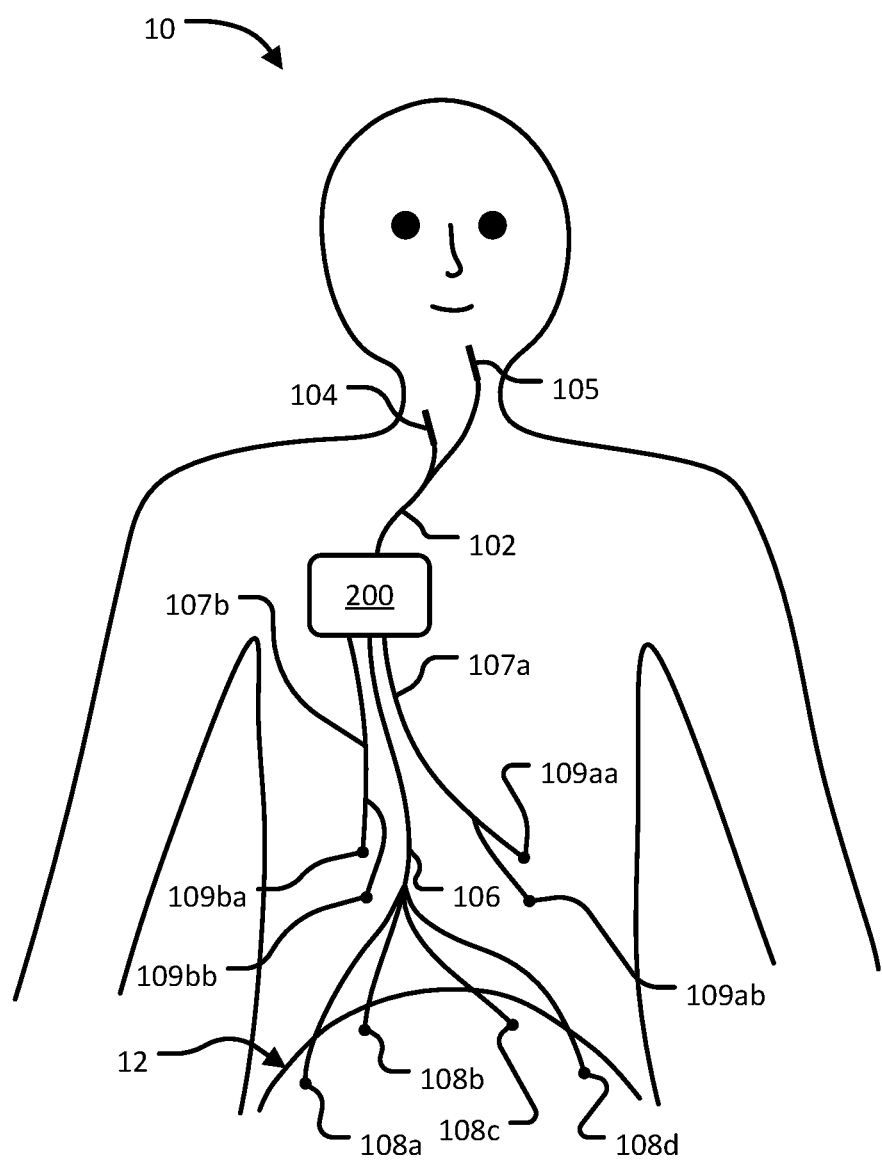
FIG. 1 is a schematic diagram of a patient with an implantable medical device for controlling breathing and/or other physiological functions, in accordance with some embodiments provided herein.

Referring to FIG. 1, a patient 10 can be implanted with an implantable medical device (IMD) 200 for controlling breathing and/or, in some embodiments, additional physiological functions such as airway clearance, speech, swallowing, voiding, and the like. In some embodiments, IMD 200 can include an upper lead 102 extending toward a first sensing electrode 104 and/or one or more second sensing electrodes 105 (optional). While the depicted embodiment of IMD 200 includes two sensing electrodes 104 and 105, in some embodiments a single sensing electrode, three sensing electrodes, four sensing electrodes, or more than four sensing electrodes are included.

In the depicted embodiment, IMD 200 also includes a first lower lead 106 extending toward one or more stimulation electrodes 108a, 108b, 108c, and/or 108d for stimulating a diaphragm 12 of the patient 10. In some embodiments, such as the depicted embodiment, one or more additional lower leads 107a-b extending toward electrodes, such as electrode pairs 109aa-ab and 190ba-bb respectively, are also optionally included. In some embodiments, the electrode pairs 109aa-ab and 190ba-bb can be used to bilaterally stimulate abdominal muscles such as, but not limited to, the rectus abdominis and/or external oblique muscles. Stimulation of such muscles can help to facilitate coughing, sneezing, voiding, and other physiological functions in some cases. In some embodiments, electrode pairs 109aa-ab and 190ba-bb can be implanted. In some embodiments, electrode pairs 109aa-ab and 190ba-bb can be located on transcutaneous patches. While the depicted embodiment includes two electrode pairs 109aa-ab and 190ba-bb that can be used to bilaterally stimulate abdominal muscles, in some embodiments four electrode pairs, or more than four electrode pairs for stimulating abdominal muscles are included. IMD 200 is more fully described with respect to FIG. 2. In some cases, lead 102, lead 106, and/or leads 107a-b can be wired leads communicably coupled to IMD 200, sensing electrodes 104 and 105, and stimulation electrodes 108a-d, 109aa-aband/or 109ba-bb. In some cases, wireless communication can be used between IMD 200 and sensing electrodes 104 and/or 105. In some cases, wireless communication be used between IMD 200 and stimulation electrodes 108a-d, 109aa-ab, and/or 109ba-bb.

In some embodiments, sensing electrode 104 can be coupled to the posterior cricoarytenoid (PCA), not shown, of patient 10. The PCA is a muscle in the larynx that is closely and cyclically coordinated with the diaphragm 12 and onset of inspiratory flow, with PCA activity preceding that of diaphragm 12. The PCA is innervated with a branch of the vagus nerve. In some cases, sensing electrode 104 can be an epimysial electrode that is fixed to a surface of the PCA via sutures or anchors. In some cases, sensing electrode 104 can be an intramuscular electrode that is fixed into the tissue of the PCA.

In some embodiments, sensing electrode 105 (which may optionally comprise two or more electrodes) can be coupled to one or more muscles that control motions of the larynx of patient 10, or to nerves associated with such muscles. For example, in some such embodiments sensing electrode 105 is arranged to detect activation of muscles such as, but not limited to the stylopharyngeus muscle, thryoarytenoid muscle, mylohyoid muscle, and the like, and combinations thereof. Such muscles are activated during functions such as swallowing and coughing. For example, the thryoarytenoid muscle, which is innervated by branches of the vagus nerve, is a muscle in the larynx that is activated during cough. The mylohyoid muscle, which is innervated by the mandibular branch of the trigeminal nerve, is a muscle in the pharynx that is activated during swallow but not during cough. Accordingly, one or more sensing electrodes 105 can be used in conjunction with IMD 200 to detect patient's 10 need or desire to perform functions such as coughing, swallowing, and the like. The one or more sensing electrodes 105 may be epimysial, intramuscular electrodes, or combinations thereof.

Stimulation electrodes 108a, 108b, 108c, and/or 108d can provide stimulation to diaphragm 12. In some cases, stimulation electrodes 108a, 108b, 108c, and/or 108d can be epimysial electrodes that are fixed to a surface of diaphragm 12 by sutures or anchors. In some cases, stimulation electrodes 108a, 108b, 108c, and/or 108d can be intramuscular electrodes that are fixed into the tissue of diaphragm 12. In some cases, all four stimulation electrodes 108a, 108b, 108c, and 108d are used. In some cases, two of the stimulation electrodes 108a, 108b, 108c, and/or 108d are located on one half of diaphragm 12 and two of the stimulation electrodes 108a, 108b, 108c, and/or 108d are location on a second half of diaphragm 12. In some cases, all four stimulation electrodes 108a, 108b, 108c, and 108d are implanted, but are individually selectable for stimulation such that all four stimulation electrodes 108a, 108b, 108c, and 108d may not be providing stimulation. The amplitude, frequency, and/or duration of stimulation delivered by stimulation electrodes 108a, 108b, 108c, and/or 108d can also be modulated in keeping with the extent or magnitude of desired or needed activation to facilitate various physiological functions (e.g., cough, sneezing, voiding, speech, swallowing, breathing, etc.).

Stimulation electrode pairs 109aa-ab and 190ba-bb can be used to bilaterally stimulate abdominal muscles such as, but not limited to, the rectus abdominis and/or external oblique muscles. In some embodiments four electrode pairs, or more than four electrode pairs are included to stimulate abdominal muscles. For example, in some embodiments, all of the abdominal activation electrode pairs (e.g., eight total electrodes) would be used to activate the expiratory muscles during the compression (second) phase of cough. In some such cases, the stimulation electrodes 108a, 108b, 108c, and 108d would simultaneously be activated along with activation of electrode pairs 109aa-ab and 190ba-bb. The amplitude, frequency, and/or duration of stimulation delivered by electrode pairs 109aa-ab and 190ba-bb, and/or stimulation electrodes 108a, 108b, 108c, and/or 108d can also be modulated in keeping with the extent or magnitude of desired or needed activation for various physiological functions. For example, in the case of cough, the stimulation electrodes 108a, 108b, 108c, and/or 108d may be activated at a higher level than the level(s) of activation for breathing (in addition to the co-activation of the electrodes that stimulate abdominal muscles in some cases).

While the depicted embodiment outputs stimulation from IMD 200 to one or more muscles of patient 10 (e.g., using electrodes 108a, 108b, 108c, 108d, and/or electrode pairs 109aa-ab and 190ba-bb), in some embodiments the output(s) from IMD 200 may be utilized for epidural stimulation. In some embodiments, IMD 200 outputs signals for a combination of muscle stimulation and for epidural stimulation.

Figure 2:
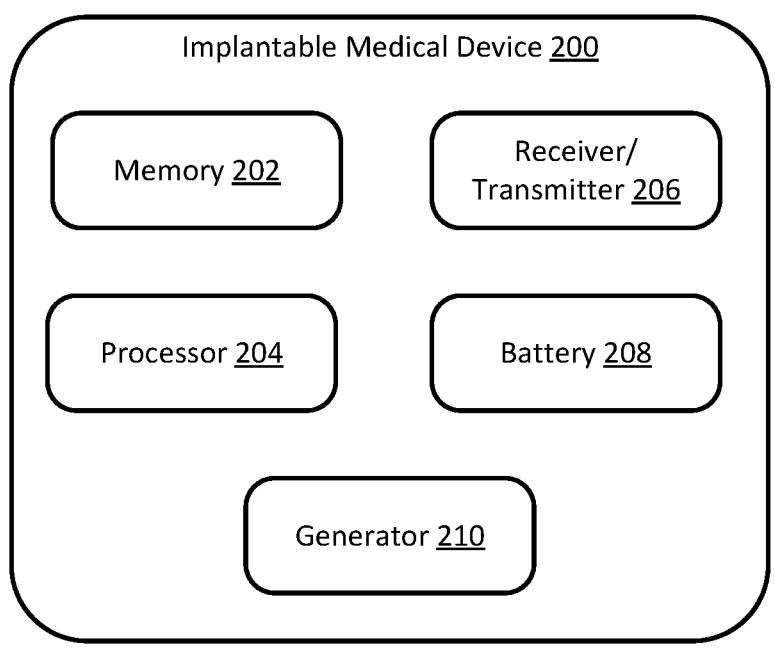
FIG. 2 is a schematic diagram of the implantable medical device of FIG. 1, in accordance with some embodiments provided herein.

Referring also to FIG. 2, IMD 200 can control breathing by providing electrical stimulation to diaphragm 12. In some cases, IMD 200 may be implanted below a clavicle of patient 10. IMD 200 can include a memory 202, a processor 204, a receiver/transmitter 206, a battery 208, and a generator 210, which can all be communicably coupled to one another. Communicably coupled can include direct communications, indirect communications, wired communications, and/or wireless communications.

Memory 202 can be a computer-readable storage medium that is capable of storing data and computer executable instructions. Memory 202 can be a variety of different types of computer-readable storage media including, but not limited to, volatile, such as RAM, non-volatile, such as ROM, flash memory, or some combination of the two. Memory 202 can store stimulation parameters.

Processor 204 can facilitate execution of the computer executable components and/or the computer executable instructions stored in memory 202. Operations of processor 204 are described in greater detail with respect to FIG. 3.

Receiver/transmitter 206 can communicate with sensing electrode 104 and/or stimulation electrodes 108a, 108b, 108c, and/or 108d. In some cases, receiver/transmitter 206 can communicate with various other devices that are external to patient 10. For example, in some embodiments receiver/transmitter 206 may communicate with a patient magnet, a programming wand, and/or a charging device. Receiver/transmitter 206 may be or include an antenna. In some cases, receiver/transmitter 206 can use radio frequency (RF) signals, Bluetooth, Wi-Fi, cellular networks, 3G, LTE, RF, or Zigbee for wireless communication. In some cases, receiver/transmitter 206 can communicate via both wired and wireless connections. In some cases, different communication techniques can be used for different components.

Battery 208 can provide power to IMD 200 and the components of IMD 200.

In some cases, battery 208 can be a lithium carbon monoflouride battery. In some cases, battery 208 can be a lithium ion battery, or another type of battery. In some cases, battery 208 includes multiple batteries. In some cases, battery 208 is rechargeable.

Generator 210 can generate electrical signals to be delivered to diaphragm 12 via stimulation electrodes 108a, 108b, 108c, and/or 108d. In some cases, stimulation parameters for the electrical signals can be stored in memory 202. In some cases, the stimulation parameters can be programmable. Each stimulation parameter can be independently programmed, or modified based on data from the sensing electrode 104, to define the characteristics of the cycles of stimulation and inhibition to ensure optimal stimulation for a patient 10. The programmable stimulation parameters can include output current, signal frequency, pulse width, signal ON time, signal OFF time, and duty cycle.

In some cases, the components described above are enclosed in a housing of IMD 200. The housing can be hermetically sealed and biocompatible. In some cases, the housing includes one or more headers to receive the leads 102 and 106.

Figure 3:
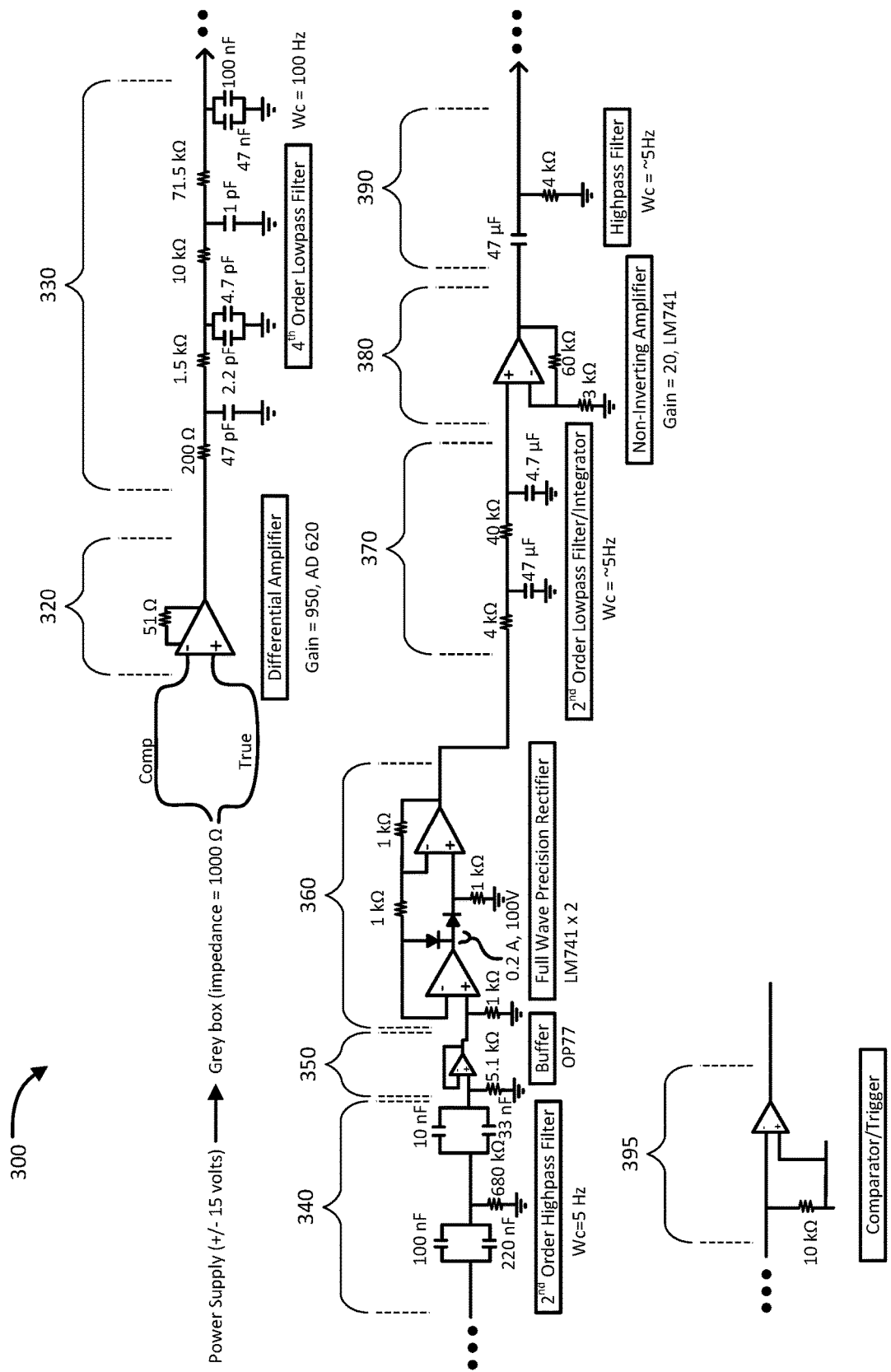
FIG. 3 is a schematic diagram of internal circuitry of a processor of the implantable medical device of FIG. 1, in accordance with some embodiments provided herein.

Referring also to FIG. 3, internal circuitry 300 of the processor 204 of the implantable medical device 200 can be configured to receive an electrical impedance signal from sensing electrode 104, and to provide a trigger signal that indicates the presence of the beginning of a breath, and a magnitude of the breath.

The circuit 300 can be configured to receive a first input signal 310a and a second input signal 310b. The first input signal 310a and the second input signal 310b can form a differential signal pair provided by a sensor electrode (not shown) configured to sense a time and magnitude of a breath. The first input signal 310a and the second input signal 310b can be received by a differential amplifier 320. In some cases, the differential amplifier 320 can include an operational amplifier configured as an instrumentation amplifier with a gain factor of about 950. The circuitry for sensing for the thryoarytenoid and mylohyoid muscles would be similar to the circuitry for sensing the PCA.

The signal, as amplified by the differential amplifier 320, can be provided to a filter 330. In some cases, the filter 330 can be a 4th order low-pass filter with a cutoff frequency of about 100 Hz. The signal, as filtered by the filter 330, can be received by a filter 340. In some cases, the filter 340 can be a 2nd order high-pass filter with a cutoff frequency of about 5 Hz. In some cases, the filter 330 and the filter 340 can be configured as, or be replaced by, a band-pass filter (e.g., passing frequencies between about 5 Hz and 100 Hz).

The signal, as filtered by the filter 340, can be buffered by a buffer amplifier 350. In some cases, the buffer amplifier 350 can transform the electrical impedance of the upstream circuit (e.g., the filtered signal provided by the filter 340) to downstream circuitry, to prevent the signal source from being affected by whatever currents that the load may produce.

The signal, as buffered by the buffer amplifier 350, can be rectified by a rectifier 360. In some cases, the rectifier 360 can be a full-wave rectifier configured to transform the provided signal from an AC waveform to a pulsating DC waveform. The signal, as rectified by the rectifier 360, can be received by a low-pass filter and integrator circuit 370. In some cases, the circuit 370 can be a $2^{nd}$ order low-pass filter and integrator circuit having a cutoff frequency of about 5 Hz.

The filtered and integrated signal, as provided by the circuit 370, can be amplified by an amplifier 380. In some cases, the amplifier 380 can be an operational amplifier configured as a non-inverting amplifier having a gain factor of about 20. The signal, as amplified by the amplifier 380, can be received by a filter 390. In some cases, the filter 390 can be a high-pass filter having a cutoff frequency of about 4 Hz or 5 Hz.

The signal, as filtered by the filter 390, can be received by a trigger circuit 395. In some cases, the trigger circuit 395 can include an operational amplifier configured as a comparator that can provide a first output voltage when breath is detected and a second, different output voltage (e.g., no voltage) when no breath is detected. The output of the trigger circuit 395 can be provided as an input to generator 210.

The configuration of circuit 300 can provide accurate breathing information throughout the length of implantation of IMD 200, even if signal quality deteriorates.

Figure 4:
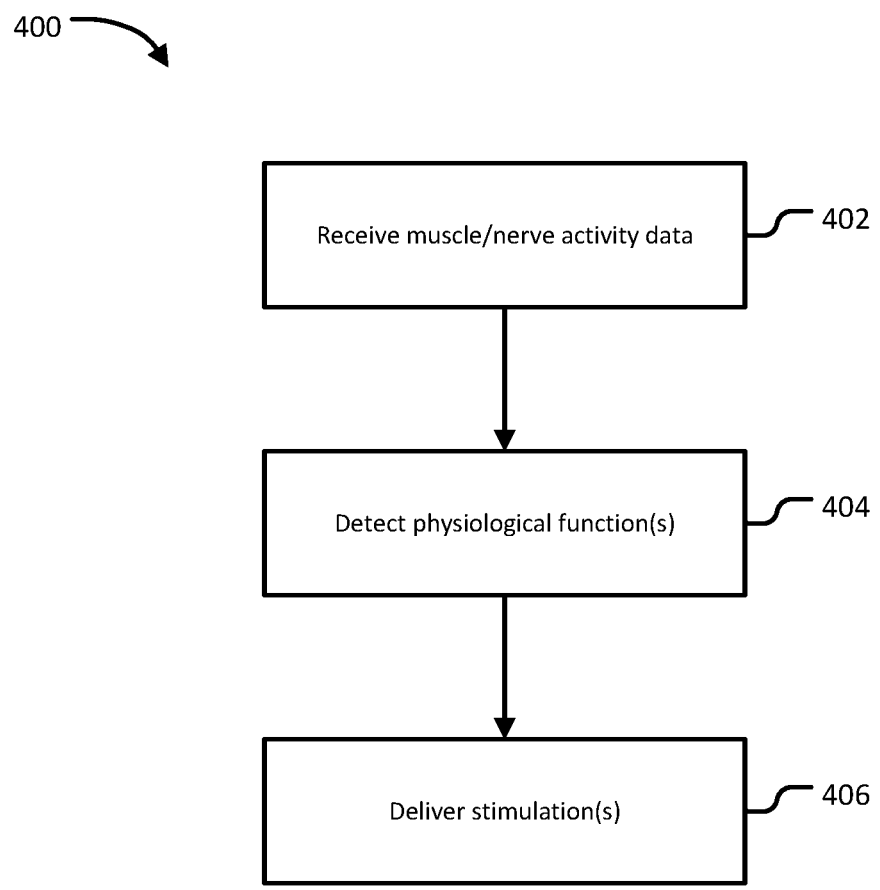
FIG. 4 is a method of controlling breathing and/or other physiological functions, in accordance with some embodiments provided herein.

Referring to FIG. 4, a method 400 of controlling breathing and/or other physiological functions can include receiving muscle/nerve activity data at operation 402, detecting physiological function(s) at operation 404, and delivering stimulation(s) at operation 406. In some embodiments, method 400 can be performed by the control system of IMD 200, and using the leads, electrodes, and sensors associated therewith.

In some embodiments, data that is indicative of muscle and/or nerve activity can be received from one or more sensing electrode(s) at operation 402. For example, data indicative of muscle and/or nerve activity associated with breathing can be electromyography (EMG) data relating to contraction and relaxation of the PCA, or electroneurography data from the nerves which supply it (ENG). In another example, data indicative of muscle and/or nerve activity associated with coughing can include EMG data relating to activation of the PCA and activation of the thyroarytenoid (or the nerves associated therewith), without activation of the mylohyoid. Other patterns of data indicative of muscle and/or nerve activity (relating to other functions such as sneezing, voiding, swallowing, speaking, and the like) can also be received at operation 402.

One or more physiological functions can be detected at operation 404 by the control system of IMD 200. For example, a breath can be detected at operation 404 by determining a point in time or an instance of contraction of the PCA from the muscle/nerve activity data received at operation 402. In some embodiments, a breath can be detected at operation 404 by determining a peak root mean squared (RMS) value of the PCA contraction from the breathing data to determine a magnitude of the breath. In some cases, detecting a breath at operation 404 can include removing artifacts from the breathing data that can be caused by coughing, chewing, movement of the neck, or swallowing. In some cases, methods for detecting a breath can be modified to account for patient 10 sleeping, as electrical activity of the PCA is different during sleep than when awake. In another example, at operation 404 coughing can be detected when the data received at operation 402 includes EMG data relating to activation of the PCA and activation of the thyroarytenoid (or the nerves associated therewith), without activation of the mylohyoid. Other physiological functions such as sneezing, voiding, swallowing, speaking, and the like can also be detected at operation 404, based on the muscle/nerve activation data received at operation 402.

Delivering stimulation from IMD 200 at operation 406 can include generating electrical signals according to stored stimulation parameters or determined stimulation parameters and delivering the electrical signals to the stimulation electrodes. The type of stimulation delivered is based on the physiological function(s) detected in operation 404. For example, when breathing is detected in operation 404, stimulation electrodes 108a, 108b, 108c, and/or 108d can be activated to stimulate motion of the patient's diaphragm muscle. In another example, when coughing is detected in operation 404, stimulation electrodes 108a, 108b, 108c, 108d and electrode pairs 109aa-ab and 190ba-bb can be activated to stimulate concurrent motion of the patient's diaphragm and abdominal muscles (e.g., rectus abdominis and external oblique muscles). Stimulation parameters of the delivered stimulation can adjustably include output current, signal frequency, pulse width, signal ON time, signal OFF time, and duty cycle. Delivering stimulation at operation 406 can be based on, or in response to, detecting a particular physiological function at operation 404. In some cases, the stimulation can be generated with a time delay. For example, in some cases the delivery of the stimulation for breathing is delayed from the onset of the detected PCA contraction to account for the delay between the PCA and diaphragm 12.

In some cases, a peak of the stimulation generated can be determined based on a ratio of the PCA contraction peak determined from the breathing data to diaphragm peak. In some embodiments, the stimulation delivered at operation 406 comprises epidural stimulation.

In some cases, breathing time can be determined and/or verified by comparing the PCA contraction to the onset of inspiration. Similarly, in some cases coughing time can be determined and/or verified by comparing PCA and thyroarytenoid activation.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can, in some cases, be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Particular embodiments of the subject matter have been described. Other embodiments are within the scope of the following claims. For example, the actions recited in the claims can be performed in a different order and still achieve desirable results. As one example, the process depicted in the accompanying figures does not necessarily require the particular order shown, or sequential order, to achieve desirable results. In certain implementations, multitasking and parallel processing may be advantageous.

What is claimed is:

1. A system for controlling breathing, the system comprising:
    a sensing electrode that senses electromyography (EMG) or electroneurogram (ENG) data from a throat muscle or nerve of a patient;
    a stimulation electrode that provides stimulation to a diaphragm of the patient; and
    an implantable medical device communicably coupled to the sensing electrode and the stimulation electrode, the implantable medical device comprising:
        a memory storing computer executable instructions; and
        a processor that is configured to execute the computer executable instructions to cause the processor to:
            receive the EMG or ENG data from the sensing electrode;
            detect an intent of the patient to take a breath based on the received EMG or ENG data;
            deliver an electrical signal to the diaphragm via the stimulation electrodes when the intent of the patient to take a breath is detected;
            detect a non-breath comprising at least one of coughing, chewing, movement of a neck, and swallowing; and
            inhibit a delivery of the electrical signal upon detecting the non-breath.

2. The system of claim 1, wherein the throat muscle is a posterior cricoarytenoid muscle.

3. The system of claim 1, wherein the intent of the patient to take a breath is detected based on an initiation of a contraction of a neck muscle of the patient.

4. The system of claim 3, wherein the electrical signal comprises an onset delay.

5. The system of claim 4, wherein the onset delay corresponds to a natural delay between the initiation of a contraction of the throat muscle and a contraction of the diaphragm during normal breathing.

6. The system of claim 1, wherein the computer executable instructions further cause the processor to determine a magnitude of a contraction of the throat muscle.

7. The system of claim 6, wherein the electrical signal comprises an amplitude and wherein the amplitude corresponds to the magnitude of the contraction of the throat muscle.

8. A method of controlling breathing, the method comprising:
    receiving, from a sensing electrode, electromyography (EMG) or electroneurogram (ENG) data from a throat muscle or a throat nerve of a patient;
    detecting, via a processor, an intent of the patient to take a breath from the EMG or ENG data;
    delivering, via a stimulation electrode, an electrical signal to a diaphragm or a phrenic nerve of the patient when the intent of the patient to take a breath is detected;
    detecting a non-breath comprising at least one of coughing, chewing, movement of a neck, and swallowing; and
    inhibiting delivery of the electrical signal upon detecting the non-breath.

9. The method of claim 8, wherein the throat muscle is a posterior cricoarytenoid muscle.

10. The method of claim 8, wherein the intent of the patient to take a breath is detected based on an initiation of a contraction of the throat muscle.

11. The method of claim 10, wherein the electrical signal comprises an onset delay.

12. The method of claim 11, wherein the onset delay corresponds to a natural delay between the initiation of the contraction of the throat muscle and a contraction of the diaphragm during normal breathing.

13. The method of claim 8, further comprising determining a magnitude of a contraction of the throat muscle.

14. The method of claim 13, wherein the electrical signal comprises an amplitude and wherein the amplitude corresponds to the magnitude of the contraction of the throat muscle.

15. An implantable medical device configured to be communicably coupled to a sensing electrode and a stimulation electrode, the implantable medical device comprising:
- a memory storing computer executable instructions; and
- a processor that is configured to execute the computer executable instructions to cause the processor to:
  - receive electromyography (EMG) or electroneurogram (ENG) data from a throat muscle or nerve of a patient;
  - detect an intent of the patient to take a breath from the EMG or ENG data;
  - deliver an electrical signal to a diaphragm of the patient when the breath is detected;
  - detect a non-breath comprising at least one of coughing, chewing, movement of a neck, and swallowing; and
  - inhibit delivery of the electrical signal upon detecting the non-breath.

16. The implantable medical device of claim 15, wherein the throat muscle is a posterior cricoarytenoid muscle.

17. The implantable medical device of claim 15, wherein the intent of the patient to take a breath is detected based on an initiation of a contraction of the throat muscle.

18. The implantable medical device of claim 17, wherein the electrical signal comprises an onset delay and wherein the onset delay corresponds to a natural delay between the initiation of the contraction of the throat muscle and a contraction of the diaphragm during normal breathing.

* * * * *